Figure 1:
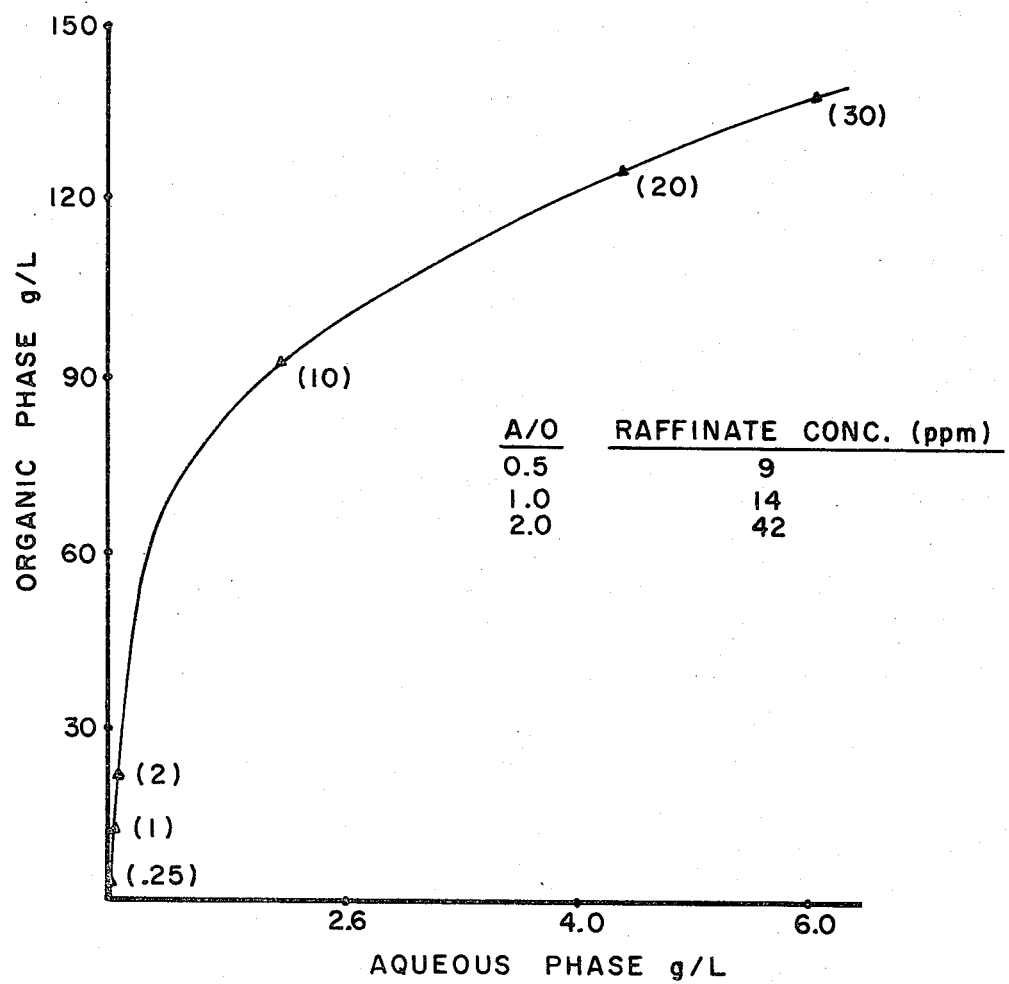

United States Patent [19]

Savides et al.

[11] 4,420,643

[45] Dec. 13, 1983

[54] EXTRACTION OF PHENOLS FROM AQUEOUS SOLUTIONS

[75] Inventors: Christos Savides, Somerville; John H. Bright, Kendall Park, both of N.J.

[73] Assignee: American Cyanamid Company, Stamford, Conn.

[21] Appl. No.: 429,907

[22] Filed: Sep. 30, 1982

[51] Int. Cl.³ .............................................. C07C 37/68
[52] U.S. Cl. ................... 568/753; 568/724; 568/742; 568/749; 568/756
[58] Field of Search ................ 568/753, 749, 724, 742

[56] References Cited

U.S. PATENT DOCUMENTS

| | | | |
|---|---|---|---|
| 3,968,171 | 7/1976 | Burkholder et al. | 568/753 |
| 4,025,423 | 5/1977 | Stonner et al. | 568/749 |
| 4,026,791 | 5/1977 | Wallace | 568/749 |
| 4,113,974 | 9/1978 | Mark et al. | 568/749 |
| 4,152,528 | 5/1979 | Strahorn | 568/749 |
| 4,294,993 | 10/1981 | Li | 568/749 |
| 4,324,926 | 4/1982 | Demler et al. | 568/749 |
| 4,325,789 | 4/1982 | Wus et al. | 568/749 |
| 4,374,283 | 2/1983 | Aneja | 568/749 |

FOREIGN PATENT DOCUMENTS

| | | | |
|---|---|---|---|
| 52-7930 | 1/1977 | Japan | 568/753 |
| 7410872 | 2/1976 | Netherlands | 568/753 |
| 923679 | 4/1963 | United Kingdom | 568/749 |
| 1538212 | 1/1979 | United Kingdom | 568/749 |
| 343970 | 8/1972 | U.S.S.R. | 568/756 |

*Primary Examiner*—Werren B. Lone
*Attorney, Agent, or Firm*—Michael J. Kelly

[57] ABSTRACT

A process for the extraction of phenolic compounds from aqueous solutions is disclosed. The process comprises contacting said aqueous solution with an organic solution comprising at least one tertiary phosphine oxide and a high boiling organic solvent.

7 Claims, 1 Drawing Figure

EXTRACTION OF 1.05 WT % PHENOL
by 325 g/L TOPO in linear alkyl benzene
A/O Ratios Are Given in ( )

| A/O | RAFFINATE CONC. (ppm) |
|---|---|
| 0.5 | 9 |
| 1.0 | 14 |
| 2.0 | 42 |

EXTRACTION OF PHENOLS FROM AQUEOUS SOLUTIONS

The present invention relates to a process for the extraction of phenols from aqueous solutions by solvent extraction. More particularly, it relates to a process for the solvent extraction of phenols using a solution of at least one tertiary phosphine oxide compound in a high boiling organic solvent. Still more particularly, it relates to the extraction of phenols from aqueous solutions using a solution of tri-n-octylphosphine oxide (TOPO) in a $C_{10}$ to $C_{16}$ alkyl-substituted aromatic hydrocarbon solvent.

Phenols occur in aqueous waste streams from many industrial processes, such as the cumene-phenol process, petroleum refining, petrochemical manufacture, coal gasification and coal liquifaction processes. When the concentration of phenol in such waste streams is high enough to pose a disposal problem or to justify recovery, the presently available recovery processes provide only limited success.

Solvent extraction processes are preferred over steam distillation processes for the extraction of phenols because the water-phenol mixture forms an azeotrope of 9.2 weight percent phenol. Common solvents for solvent extraction are diisopropyl ether (DIPE), used in the Phenolsolvan process, and methyl isobutyl ketone (MIBK), used in the Chem-Pro counter-current column process. Recovery of phenol via these processes requires distillation of the solvent-phenol solution to remove the more volatile solvents before the phenol can be isolated. Thus, there is a need for a more efficient solvent extraction process for phenols, preferably one in which the extracted phenols can be recovered simply and directly without the necessity of distilling large quantities of solvent.

The present invention is based on the discovery of a highly efficient solvent extraction process for the recovery of phenols from aqueous waste streams, which process comprises contacting said aqueous phenol-containing waste stream with a solution of a tertiary phosphine oxide compound, represented by the formula:

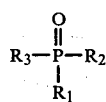

wherein $R_1$, $R_2$, and $R_3$ individually represent alkyl groups containing from 1 to 20 carbon atoms, provided that at least two of said R groups contain 6 or more carbon atoms, in a $C_{10}$ to $C_{16}$ alkyl-substituted aromatic hydrocarbon having a high boiling point, that is a boiling point of at least about 200° C.; separating the organic phase from the aqueous phase, and distilling said phenol from said organic phase.

The process of the present invention has the advantage of providing highly efficient extraction of phenols from aqueous solutions, giving very high equilibrium distribution coefficients, and also permitting direct recovery of the extracted phenol from the organic solution by distillation, and recycling of the organic solvent containing the phosphine oxide extractant.

The extraction of phenol from aqueous solutions using phosphine oxides, particularly TOPO, in an organic solvent, for example, diisobutylketone (DIBK), is known; see MacGlashan, M.S. Thesis, University of California (Berkeley), March, 1982. The use of diisobutylketone, however, requires the distillation of the lower boiling solvent before the phenol can be recovered. This, of course, negates any possibility of recycle of the extractant solution.

In accordance with the process of the present invention, a waste stream containing one or more phenolic compounds dissolved in water is contacted, by any convenient conventional techniques used in solvent extraction processes, with a solution of a tertiary phosphine oxide in a high boiling organic solvent, preferably an alkyl-substituted aromatic hydrocarbon. When aqueous/organic phases disengage, the organic phase, containing the extracted phenolic compound(s), may then be subjected to distillation to remove the phenolic compound from the solution. The organic solution remaining, which contains the tertiary phosphine oxide, is then recycled to another extraction stage. It is recognized that any convenient means of separating the phenol from the organic phase would be equally applicable.

In waste streams containing phenolic compounds, phenol is usually the major constituent among those present. Other phenolic compounds may be present in lesser amount, but may be more difficult to extract from the waste stream, for example, di- and trihydroxyaromatic compounds. These compounds are readily removed according to the process of the present invention and generally most phenolic compounds of concern to the environment toxicity problems may be extracted to levels below what is now considered to be acceptable. Phenolic compounds which are extracted from aqueous waste streams include, for example, phenol, $C_1$–$C_2$ alkyl-substituted phenols, such as o-, m- and p-cresol, the xylenols, p-ethylphenol; dihydric phenols, such as hydroquinone, catechol, resorcinol, monoethers thereof, such as o-methoxyphenol; trihydric phenols, such as phloroglucinol, pyrogallol, and mono- and diethers thereof; naphthols, and the like.

To be extracted, the phenols should not be in salt form. Therefore, it may be necessary to neutralize aqueous solutions containing dissolved phenolates before extraction. This can be readily accomplished by the addition of a mineral acid.

The phosphine oxides which are usefully employed are those represented by the formula:

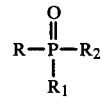

wherein R, $R_1$, and $R_2$ individually represent alkyl groups containing from 1 to 20 carbon atoms, provided that at least two of said R groups contain 6 or more carbon atoms. The term "alkyl group," as used herein, includes cycloalkyl, such as cyclohexyl. Such tertiary phosphine oxides include tri-n-hexyl phosphine oxide, tri-n-heptylphosphine oxide, tri-n-octylphosphine oxide, triisooctylphosphine oxide, tri-n-decylphosphine oxide, tri-n-dodecylphosphine oxide, tri-n-hexadecylphosphine oxide, tri-n-octadecylphosphine oxide, trieicosylphosphine oxide, tris(2,4,4-trimethylpentyl)-phosphine oxide, di-n-hexylmethylphosphine oxide, dicyclo-hexyloctylphosphine oxide, di-n-octylmethylphosphine oxide, di-n-octylisobutylphosphine oxide, dicyclohexyloctylphosphine oxide, didecylmethylphosphine oxide, di-n-hexylisobutylphosphine oxide, dicyclooctylethylphosphine oxide, di-n-hexyldodecylphosphine oxide, and the like. The preferred phosphine oxide is tri-n-octylphosphine oxide (TOPO).

The extractant composition of the present invention comprises a solution of at least one phosphine oxide compound dissolved in an organic solvent having a boiling point of at least about 200° C., preferably above about 240° C. Preferred organic solvents include alkyl-substituted aromatic hydrocarbons. Preferred alkyl-substituted aromatic hydrocarbons are the $C_{10}$ to $C_{16}$ alkyl-substituted benzenes and mixtures thereof. A particularly useful hydrocarbon solvent is Nalkylene 550 (Conoco), a linear alkyl benzene having a boiling point above 280° C. This solvent is a mixture of $C_{10}$ to $C_{14}$ alkyl benzenes. Other useful solvents include isopropyl naphthalene, diisopropyl naphthalene, and the like.

It is advantageous in solvent extraction to maximize the loading of the extracted compound in the organic phase. This also permits a higher ratio of aqueous phase to organic phase (A/O) in the extraction process, that is, a greater volume of aqueous solution treated per volume of organic extractant. It is therefore desirable to maximize the concentration of phosphine oxide in the extraction solution. With TOPO, solutions containing in excess of 30% by weight are readily obtained.

The aqueous solution is contacted in a liquid-liquid extraction process, either by batch, continusouly co-current or continuously counter current, with the organic extraction solution. The ratio of aqueous (A) to organic (O) phase is chosen to most efficiently remove the phenolic compounds from solution. Aqueous to organic (A/O) ratios of 1:30 to 30:1 are believed to be effective, although other ratios may prove to be effective depending on the specific separation. These ratios are not particularly critical to the instant invention and the desired ratios are primarily a function of economic performance and convenience.

A McCabe-Thiele diagram (FIG. 1) was prepared from data obtained in the extraction of 1.05% aqueous solutions of phenol with a solution of 325 g/l of TOPO in linear alkyl benzene. From the diagram, assuming an aqueous phenol concentration of 1.58%, and using an A/O=7.5 operating line, requiring a material balance loading of 118.5 g/l of phenol (15.8 g/l×7.5=118.5 g/l), it is determined that three counter-current stages would reduce the phenol content to about 5 ppm, well below the 100 ppm requirement for disposal. Recovery of the phenol is achieved by direct distillation of the phenol from the linear alkyl benzene solution. The extractant is then recycled to the extraction stage.

The following examples are provided for illustrative purposes only and are not meant to limit the scope of the invention, which scope is set forth in the claims to follow.

EXAMPLE 1

A 1% aqueous solution of phenol was shaken with a solution of tri-n-octylphosphine oxide (TOPO) in a $C_{10}$-$C_{14}$ linear alkyl benzene for 10 minutes at 25° C. using an aqueous/organic (A/O) ratio of 1. The aqueous layer was analyzed for phenol content by U.V. spectroscopy and the equilibrium distribution coefficient ($K_D$) was calculated. The experiment was repeated using diisobutylketone (DIBK) as solvent instead of Conoco 550. Data are given in Table I.

TABLE I

| Diluent | Boiling Pt. °C. | TOPO (g/l) | $K_D$ |
|---|---|---|---|
| $C_{10}$-$C_{14}$ linear alkyl benzene | >280 | 133 | 250 |
| $C_{10}$-$C_{14}$ linear alkyl benzene | >280 | 325 | 616 |
| $C_{10}$-$C_{14}$ linear alkyl benzene | >280 | None | 0.4 |
| DIBK | 168 | 133 | 171 |
| DIBK | 168 | None | 35 |

In Table I $K_D = (C\ org./C\ aq.)$

C org. = concentration phenol in organic phase
C aq. = concentration phenol in aqueous phase.

The data show that the $C_{10}$-$C_{14}$ linear alkyl benzene, which alone is less efficient than DIBK ($K_D$ 0.4 vs 35), is surprisingly more efficient than DIBK in the presence of TOPO.

EXAMPLE 2

An aqueous solution of 1% hydroquinone was shaken with a 325 g/l solution of TOPO in the alkyl benzene of Example 1 at 25° C. using an A/O ratio of 1. The distribution coefficient $K_D$ was 80 in the presence of TOPO and only 0.05 when the alkyl benzene was used alone.

A similar aqueous solution containing 1.37% phloroglucinol was extracted in the same manner. The distribution coefficient $K_D$ was 76 vs 0.04 without TOPO. The data are summarized in Table II.

TABLE II

| | $K_D$ (A/O = 1) | |
|---|---|---|
| | $C_{10}$-$C_{14}$ linear alkyl benzene | $C_{10}$-$C_{14}$ linear alkyl benzene + TOPO |
| Hydroquinone (1.03%) | 0.04 | 80 |
| Phloroglucinol (1.37%) | 0.04 | 76 |

The data show that TOPO in a linear alkyl benzene is a very efficient extractant for polyhydric phenols.

EXAMPLE 3

A number of high boiling solvents, which would allow recovery of the extracted phenol without the necessity of distilling the solvent, were evaluted and the distribution coefficient calculated for the solvent alone and containing 133 g/l of TOPO. The aqueous solution extracted contained 1% phenol, which was contacted with the solvent or solvent plus TOPO for 10 minutes at 24° C. Data are given in Table III.

TABLE III

| | | Alone (A/O = 1) | | Solvent + TOPO (A/O = 1) | | Solvent + TOPA (A/O = 0.5) | |
|---|---|---|---|---|---|---|---|
| Solvent | B.p. °C. | C aq. Final | $K_D$ | C aq. Final | $K_D$ | C aq. Final | $K_D$ |
| $C_{10}$-$C_{14}$ linear alkyl benzene | >284 | 7480 ppm | 0.4 | 41 | 250 | 17 | 605 |
| Isopropyl naphthalene | >259 | 4690 | 1.2 | 45 | 228 | 18 | 571 |
| Diisopropyl naphthalene | >259 | 5590 | 0.8 | 46 | 223 | 18 | 560 |
| Diphenyl ether | 258 | 3075 | 2.3 | 55 | 186 | 23 | 447 |
| Diphenyl methane | 264 | — | 59 | 59 | 170 | 21 | 480 |
| Benzophenone | 306 | — | 85 | 85 | 120 | 37 | 277 |

TABLE III-continued

| Solvent | B.p. °C. | Alone (A/O = 1) C aq. Final | $K_D$ | Solvent + TOPO (A/O = 1) C aq. Final | $K_D$ | Solvent + TOPA (A/O = 0.5) C aq. Final | $K_D$ |
|---|---|---|---|---|---|---|---|
| Tridecanol | 233 | 531 | 18 | 515 | 19 | 128 | 79 |
| Methyl isobutyl ketone | 117 | 130 | 81 | 43 | 248 | 24 | 445 |
| Aromatic 150[1] | >184 | 4450 | 1.3 | 48 | 214 | 20 | 514 |
| Kermac 470B[2] | >207 | 8000 | 0.2 | 49 | 209 | 20 | 514 |
| Diisobutyl ketone | 168 | 285 | 35 | 60 | 171 | 26 | 395 |
| Diisopropyl ether | 68 | 419 | 23 | — | — | — | — |

[1]Exxon aromatic hydrocarbon
[2]Mixture of linear and cycloaliphatic hydrocarbons: Kerr McGee The data in Table III show that the alkyl benzene, isopropyl naphthalene and diisopropyl naphthalene, which are inefficient when used alone, are surprisingly efficient in the presence of TOPO at A/O ratios of 0.5 and 1.0. Moreover, they are high boiling, permitting distillation of the phenol, and all have negligible water solubility.

What is claimed is:

1. A process for the extraction of at least one mono- or polyhydric phenolic compound from aqueous solutions which comprises: (a) contacting said aqueous solution with an organic solution comprising (i) at least one tertiary phosphine oxide compound, represented by the formula:

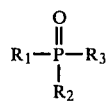

wherein $R_1$, $R_2$, and $R_3$ individually represent alkyl groups containing from 1 to 20 carbon atoms, provided that at least two of said R groups contain 6 or more carbon atoms, and (ii) a $C_{10}$ to $C_{16}$ alkyl-substituted aromatic hydrocarbon having a boiling point of at least about 200° C.; and (b) separating the organic phase from the aqueous phase.

2. The process of claim 1 wherein said phosphine oxide is tri-n-octylphosphine oxide.

3. The process of claim 1 wherein said $C_{10}$ to $C_{16}$ alkyl-substituted aromatic hydrocarbon is selected from linear alkyl benzenes, isopropyl naphthalene and diisopropyl naphthalene.

4. The process of claims 1, 2, or 3 wherein said aromatic hydrocarbon is a $C_{10}$ to $C_{14}$ linear alkyl benzene having a boiling point above 280° C.

5. The process of claim 1 wherein said phenolic compound is phenol.

6. The process of claim 5 wherein, following separation of the organic phase from the aqueous phase, the phenol is recovered from the organic phase by distillation.

7. The process of claim 6 wherein the organic phase, following distillation of the phenol, is recycled to the extraction stage.

* * * * *